United States Patent [19]
Hallinan et al.

[11] Patent Number: 5,919,787
[45] Date of Patent: Jul. 6, 1999

[54] AMINOTETRAZOLE DERIVATIVES USEFUL AS NITRIC OXIDE SYNTHASE INHIBITORS

[75] Inventors: E. Ann Hallinan, Evanston; Donald W. Hansen, Jr., Skokie; Sofya Tsymbalov, Des Plaines, all of Ill.

[73] Assignee: G. D. Searle & Co., Chicago, Ill.

[21] Appl. No.: 09/166,036

[22] Filed: Oct. 5, 1998

Related U.S. Application Data

[63] Continuation of application No. 08/817,971, Apr. 30, 1997, Pat. No. 5,854,251, which is a continuation of application No. PCT/US95/14001, Nov. 8, 1995, which is a continuation-in-part of application No. 08/336,596, Nov. 9, 1994, Pat. No. 5,684,008.

[51] Int. Cl.$^6$ ............... A61K 31/41; A61K 31/415; C07D 257/06; C07D 231/40
[52] U.S. Cl. ............... 514/256; 514/371; 514/381; 514/383; 514/398; 514/407; 544/322; 548/262.8; 548/195; 548/332.5; 548/371.7
[58] Field of Search .................. 514/256, 371, 514/381, 383, 398, 407; 544/322; 548/262.8, 195, 332.5, 371.7

[56] References Cited

U.S. PATENT DOCUMENTS

| | | | |
|---|---|---|---|
| 4,713,369 | 12/1987 | Stüber | 514/18 |
| 5,059,712 | 10/1991 | Griffith | 562/560 |
| 5,081,148 | 1/1992 | Braquet et al. | 514/162 |
| 5,132,453 | 7/1992 | Griffith | 562/560 |
| 5,196,450 | 3/1993 | Sjoerdsma et al. | 514/565 |
| 5,273,875 | 12/1993 | Griffith | 435/1 |
| 5,281,627 | 1/1994 | Griffith | 514/565 |
| 5,362,744 | 11/1994 | Purchase, Jr. et al. | 514/381 |
| 5,364,881 | 11/1994 | Griffith et al. | 514/508 |
| 5,464,858 | 11/1995 | Griffith et al. | 514/399 |

FOREIGN PATENT DOCUMENTS

| | | |
|---|---|---|
| 0370320 | 5/1990 | European Pat. Off. |
| 0446699 | 9/1991 | European Pat. Off. |
| 2240041 | 7/1991 | United Kingdom |
| 91/04023 | 4/1991 | WIPO |
| 91/04024 | 4/1991 | WIPO |
| 93/13055 | 7/1993 | WIPO |
| 93/16721 | 9/1993 | WIPO |
| 93/24126 | 12/1993 | WIPO |
| 94/14780 | 7/1994 | WIPO |
| 95/00505 | 1/1995 | WIPO |
| 95/11014 | 4/1995 | WIPO |
| 96/06076 | 2/1996 | WIPO |

OTHER PUBLICATIONS

Gould et al., "Nucleoside Intermediates in Blasticidin S Biosynthesis Identified by the In Vivo Use of Enzyme Inhibitors", *Can. J. Chem.*, vol. 72, pp. 6–11, 1994.

Tsunematsu et al., "β–Naphthylamides of Guanidinophenyl Amino Acids as Substrates of Aminopeptidases", *Chem. Pharm. Bull.*, vol. 36, No. 3, pp. 1205–1209, 1988.

Funabashi et al., "A New Anti–MRSA Dipeptide, TAN–1057 A", *Tetrahedron*, vol. 49, No. 1, pp. 13–28, 1993.

Prabhakaran et al., "Studies on Nitrogen Metabolism Using $^{13}$C NMR Spectroscopy.5.$^1$ Metabolism of L–α–Arginine in the Biosynthesis of Blasticidin S", *Tetrahedron*, vol. 27, No. 33, pp. 3815–3818, 1986.

Palacios, et al., "Nitric Oxide from L–Arginine Stimulates the Soluble Guanylate Cyclase in Adrenal Glands", *Biochemical and Biophysical Research Communications*, vol. 165, No. 2, pp. 802–809, 1989.

Knowles et al., "Kinetic Characteristics of Nitric Oxide Synthase from Rat Brain", *Biochem. J.*, vol. 269, pp. 207–210, 1990.

Chemical Abstracts, 107:40336y, 1987.
Chemical Abstracts, 63:5641d, 1965.
Chemical Abstracts, 97:38442m, 1982.
Chemical Abstracts, 76:43768t, 1972.
Chemical Abstracts, 118:72838g, 1993.
Chemical Abstracts, 64:17593h, 1966.
Chemical Abstracts, 115:29868t, 1991.
Chemical Abstracts, 104:202858, 1986.

Stuehr et al., "Mammalian Nitric Oxide Synthases" 287–347.

Plapp et al., *Analytical Biochem* 62:291–294 (1974).

Proudfoot et al., *J. Biol Chem* 264 No. 15:8764–8770 (1989).

D.D. Rees, *Br. J. Pharmacol.* 101 No. 3:746–752 (1990).

Plapp et al., *Anal. Biochem* 62 No. 1:291–294 (1974).

*Primary Examiner*—Fiona T. Powers
*Attorney, Agent, or Firm*—Alan L. Scrivner; Dennis A. Bennett

[57] ABSTRACT

The current invention discloses aminotetrazole derivatives useful as nitric oxide synthase inhibitors.

10 Claims, No Drawings

AMINOTETRAZOLE DERIVATIVES USEFUL AS NITRIC OXIDE SYNTHASE INHIBITORS

This application is a continuation of application Ser. No. 08/817,971 filed Apr. 30, 1997, now U.S. Pat. No. 5,854,251, which is a continuation of a 371 of PCT/US95/14001 filed Nov. 8, 1995, which is a continuation-in-part of application Ser. No. 08/336,596, filed Nov. 9, 1994, now U.S. Pat. No. 5,684,008.

BACKGROUND OF THE INVENTION

1. Field of the Invention

The present invention relates to aminotetrazole derivatives and their use in therapy, in particular their use as nitric oxide synthase inhibitors.

2. Related Art

It has been known since the early 1980's that the vascular relaxation brought about by acetycholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active metabolite of amylnitrite, glyceryltrinitrite and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al. *Biochemical Pharmacology.* 38, 1709–1715 (1989) and Moncada et al. *Pharmacological Reviews,* 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis, inflammatory bowel disease, cardiovascular ischemia, diabetes, hyperalgesia (allodynia), cerebral ischemia (both focal ischemia, thrombotic stroke and global ischemia, secondary to cardiac arrest), other central nervous system disorders mediated by NO and other disorders mediated by NO.

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use.

WO94/12165, WO94/14780, WO93/13055, EP0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In a broad aspect, the present invention is directed to inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering.

Compounds of the present invention are represented by the following chemical formula:

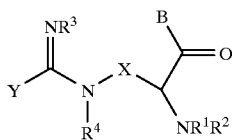

(I)

and pharmaceutically acceptable salts thereof;
wherein;

$R^1$, $R^2$ are independently selected from the group consisting of hydrogen, lower alkyl, lower alkenyl and lower alkynyl;

$R^3$, $R^4$ are independently selected from the group consisting of hydrogen, lower alkyl, lower alkenyl, lower alkynyl, $OR^6$ where $R^6$ is hydrogen, lower alkyl, lower alkenyl, lower alkynyl, aryl, $COR^7$, or $SO_2R^8$ where $R^7$ and $R^8$ are independently selected from the group consisting of lower alkyl, lower alkenyl, lower alkynyl and aryl;

X is selected from the group consisting of lower alkyl, lower alkenyl, and lower alkynyl all of which may be optionally substituted with lower alkyl, lower alkoxy, hydroxy, halogen, trifluoromethyl, nitro, cyano, amino, —$(CH_2)_pQ(CH_2)_r$— where p is 1 to 3, r is 1 to 3 and Q is oxygen, C=O, S(O)$_t$ where t is 0 to 2, or $NR^{12}$ where $R^{12}$ is hydrogen or lower alkyl which may be optionally substituted with lower alkyl, lower alkoxy, hydroxy, halogen, trifluoromethyl, nitro, cyano, amino, or —$(CH_2)_sA(CH_2)_v$— where s is 0 to 2, v is 0 to 2 and A is a 3 to 6 membered carbocyclic radical which may be optionally substituted with lower alkyl, lower alkoxy, hydroxy, halogen, trifluoromethyl, nitro, cyano, amino wherein all said radicals are optionally substituted with hydrogen, halogen and lower alkyl; or X is selected from the group of the formula —$(CH_2)_pQ(CH_2)_r$— where p is 1 to 3, r is 1 to 3 and Q is oxygen, C=O, S(O)$_t$ where t is 0 to 2, or $NR^{12}$ where $R^{12}$ is hydrogen or lower alkyl which may be optionally substituted with lower alkyl, lower alkoxy, hydroxy, halogen, trifluoromethyl, nitro, cyano, amino; or X is selected from the group of formula —$(CH_2)_sA(CH_2)_v$— where s is 0 to 2, v is 0 to 2 and A is a 3 to 6 membered carbocyclic radical which may be optionally substituted with lower alkyl, lower alkoxy, hydroxy, halogen, trifluoromethyl, nitro, cyano, amino wherein all said radicals are optionally substituted with hydrogen, halogen and lower alkyl;

Y is selected from the group consisting of lower alkyl, lower alkenyl, and lower alkynyl or Y can be $NR^9R^{10}$ wherein $R^9$ and $R^{10}$ are independently selected from the group consisting of hydrogen, lower alkyl, lower alkenyl, lower alkynyl, nitro, amino, aryl, and lower alkaryl; and B is $NR^5R^{11}$ wherein $R^5$ is selected from the group consisting of hydrogen, lower alkyl, lower alkenyl, lower alkynyl and aryl, and $R^{11}$ is selected from a 3 to 8 member heterocyclyl radical in which at least one member of the ring is carbon and in which 1 to about 4 members are heteroatoms independently selected from oxygen, nitrogen and sulfur and said heterocyclyl radical may be optionally substituted with hydroxyl, lower alkoxy, lower alkyl, halogen, nitro, carboxyl, $SO_2R^{13}$ where $R^{13}$ is selected from lower alkyl, lower alkoxy, $NR^1R^2$, amino, acyloxy, trifluoromethyl, phenyl and naphthyl which may be optionally substituted with halogen, nitro, lower alkoxy, and lower alkyl.

It is an object of the present invention to provide compounds that have usefulness as inhibitors of nitric oxide synthase. These compounds also preferentially inhibit the inducible form over the constitutive form by at least 3 fold.

It is an advantage of the present invention that the compounds are more selective than those known in the art.

It is an object of the present invention to provide compounds that also are more selective than those known in the art.

It is also an advantage in that the compounds of the present invention have preferred physical properties as compared to compounds known in the art. For example, the compound disclosed in Example 1 is a crystalline product as are all of its intermediates. In contrast, NIL, which is disclosed in WO 93/13055 when the hydrochloride salt can be isolated as a colorless crystal, but has the property of deliquescence. The compound quickly becomes a very viscous sticky oil upon exposure to moisture in normal room air which makes it difficult to handle.

A prefered compounds of the present invention are a compounds having the formula;

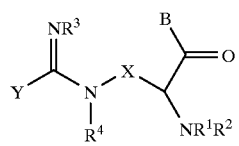

(I)

and pharmaceutically acceptable salts thereof;
wherein;

$R^1$, $R^2$ are independently selected from the group consisting of hydrogen, lower alkyl, lower alkenyl and lower alkynyl;

$R^3$, $R^4$ are independently selected from the group consisting of hydrogen, lower alkyl, lower alkenyl, lower alkynyl, $OR^6$ where $R^6$ is hydrogen, lower alkyl, lower alkenyl, lower alkynyl, aryl, $COR^7$, or $SO_2R^8$ where $R^7$ and $R^8$ are independently selected from the group consisting of lower alkyl, lower alkenyl, lower alkynyl and aryl;

X is selected from the group consisting of lower alkyl, lower alkenyl, and lower alkynyl which may be optionally substituted with lower alkyl, lower alkoxy, hydroxy, halogen, trifluoromethyl, nitro, cyano, amino, or X is selected from the group of the formula —$(CH_2)_pQ(CH_2)_r$— where p is 1 to 3, r is 1 to 3 and Q is oxygen, C=O, S(O)$_t$ where t is 0 to 2, or $NR^{12}$ where $R^{12}$ is hydrogen or lower alkyl which may be optionally substituted with lower alkyl, lower alkoxy, hydroxy, halogen, trifluoromethyl, nitro, cyano, amino; or X is selected from the group of formula —$(CH_2)_sA(CH_2)_v$— where s is 0 to 2, v is 0 to 2 and A is a 3 to 6 membered carbocyclic radical which may be optionally substituted with lower alkyl, lower alkoxy, hydroxy, halogen, trifluoromethyl, nitro, cyano, amino wherein all said radicals are optionally substituted with hydrogen, halogen and lower alkyl;

Y is selected from the group consisting of lower alkyl, lower alkenyl, and lower alkynyl or Y can be $NR^9,R^{10}$ wherein $R^9$ and $R^{10}$ are independently selected from the group consisting of hydrogen, lower alkyl, lower alkenyl, lower alkynyl, nitro, amino, aryl, and lower alkaryl; and B is $NR^5R^{11}$ wherein $R^5$ is selected from the group consisting of hydrogen, lower alkyl, lower alkenyl, lower alkynyl and aryl, and $R^{11}$ is selected from a 3 to 8 member heterocyclyl radical in which at least one member of the ring is carbon and in which 1 to about 4 members are heteroatoms independently selected from oxygen, nitrogen and sulfur and said heterocyclyl radical may be optionally substituted with hydroxyl, lower alkoxy, lower alkyl, halogen, nitro, carboxyl, amino, acyloxy, trifluoromethyl, phenyl and naphthyl which may be optionally substituted with halogen, nitro, lower alkoxy, and lower alkyl.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, ptoluenesulphonic, benzenesulphonic and isethionic acids. Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "heterocyclic radical" means an unsaturated cyclic hydrocarbon radical with 3 to about 6 carbon atoms, wherein 1 to about 4 carbon atoms are replaced by nitrogen, oxygen and/or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazonyl, quinolinyl, and the like.

The term "aryl" means an aromatic hydrocarbon radical of 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The terms "cycloalkyl" or "cycloalkenyl" means an "alicyclic radical" in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "halogen" means fluorine, chlorine, bromine or iodine.

The term "prodrug", refers to a compound that is made more active in vivo.

As used herein, reference to "treatment" of a patient is intended to include prophylaxis.

All references, patents or applications, U.S. or foreign, cited in the application are hereby incorporated by reference as if written herein.

The following general synthetic sequence is useful in making the present invention.

Scheme 1

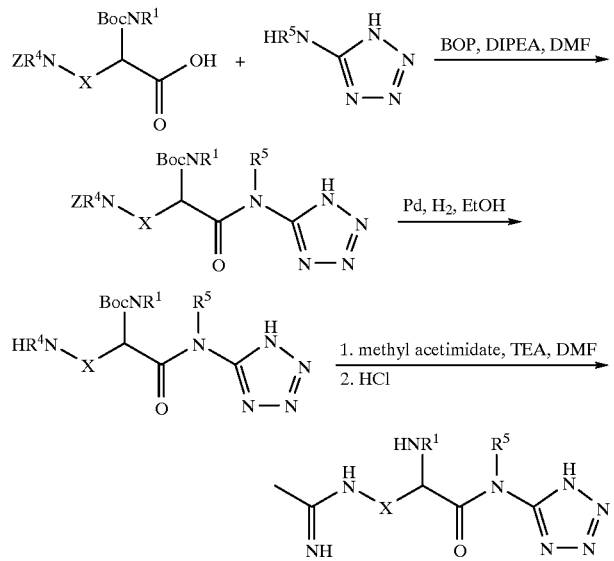

Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous $Na_2SO_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2 N in MeOH, or 6 N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. $^1$H NMR spectra were obtained from either General Electric QE-300 or Varian VXR 400 MHz spectrometer with tetramethylsilane as an internal standard. $^{13}$C NMR spectra were obtained from a Varian spectrometer at 125.8 MHz with tetramethylsilane as an internal standard.

EXAMPLE 1

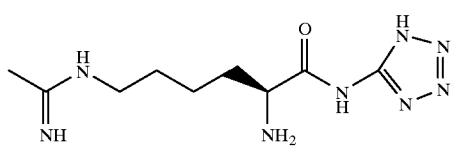

2S-amino-6-[(1-iminoethyl)amino]-N-(1H-tetrazol-5-yl)hexanamide, hydrate, dihydrochloride 1A To a stirring solution of Boc-L-Lys(Cbz)-OH (5 g, 13.18 mmol), 5-aminotetrazole monohydrate (1.36 g, 13.18 mmol) and N,N-diisopropylethylamine (DIPEA) (5.1 g, 6.9 mL, 39.54 mmol) in 20 mL of dimethylformamide (DMF) at ambient temperature was added benzotriazol-1-yl-oxy-tris-(dimethylamino)phosphonium hexafluorophosphate (BOP) (6.4 g, 14.49 mmol).

After being stirred for 1 h, the reaction mixture was concentrated under vacuum. The residue was distributed between 60 mL of ethyl acetate (EtOAc) and 50 mL of water. The layers were separated. The organic layer was washed with 50 mL of 1M $KHSO_4$ solution and 2 times with 50 mL of water. The product started to precipitate and the suspension was concentrated in vacuum giving 9 g of crude compound. After drying, the product was purified by boiling in methylene chloride followed by filtration, giving 3.7 g of 1A (62.7%). The compound was characterized by $^1$H NMR.

1B 1A (2 g, 4.5 mmol) was reduced under catalytic hydrogenation conditions using Pd black at 5 psi in 50% EtOH/AcOH solution for 12 h, giving 1.55 g (100%) of 1B. The compound was characterized by $^1$H NMR.

1C To a stirring solution of 1B (1.55 g, 4.15 mmol) and methyl acetimidate hydrochloride (0.91 g, 8.31 mmol) in 25 mL of DMF was added triethylamine (TEA) (1.26 g, 1.74 mL, 12.45 mmol). After being stirred 16 h at ambient temperature, the reaction mixture was filtered from triethylamine hydrochloride and the filtrate was concentrated in vacuum. The residue was dissolved in 50% AcOH and lyophilized. The crude product (2 g) was purified using reverse-phase chromatography on a C-18 column giving 0.9 g (52.3%) of 1C. The product was characterized by $^1$H NMR.

1 1C (0.9 g, 2.17 mmol) was dissolved in 30 mL of acetic acid and 3 mL of 4 N HCl/dioxane were added. The reaction was stirred for 20 min. at ambient temperature then 150 mL of ethyl ether were added. After 2 h, the precipitate was filtered, washed with ethyl ether, and dried giving 0.78 g of 1 (96%). Anal. Calcd. for $C_9H_{18}N_8O,2HCl, 1.25H_2O$: C,30.91; H, 6.48; N, 32.04; Cl, 20.27. Found: C, 31.64; H, 6.43; N, 32.19; Cl, 20.19. DSC mp 144.9° C.

Example 1 is also more selective than NIL. Example 1 is a nicely crystalline product as are all its intermediates. In contrast, NIL is a gum which makes it difficult to handle.

EXAMPLE 2

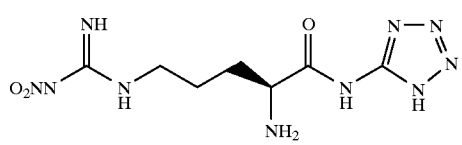

2S-amino-5-[[amino(nitroimino)methyl]amino]-N-(1H-tetrazol-5-yl)pentanamide, hydrochloride

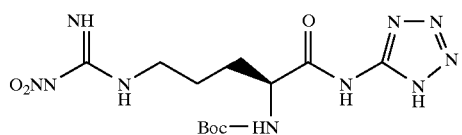

2A A sample of t-Boc nitroarginine (5.0 g, 15.6 mmol) and N-methylmorpholine (1.6 g, 15.6 mmol) dissolved in a mixture of methylene chloride ($CH_2Cl_2$, 25 mL) and DMF (25 mL) were cooled to −78° C. To this reaction stirred under a nitrogen ($N_2$) atmosphere was added isobutyl chloroformate (Aldrich, 2.2 g, 15.6 mmol). After allowing the reaction to warm to 0° C., it was maintained at this temperature for 30 min. before it was again cooled to −78° C. A sample of 5-aminotetrazole monohydrate (Aldrich, 1.62 g, 15.8 mmol) was added to the reaction mixture. The reaction was allowed to warm to room temperature and stir for 48 h. All solvent was removed under reduced pressure and the residue was partitioned between ethyl acetate (EtOAc) and water. The aqueous layer was stripped of all water and the title material was isolated from the crude product residue (9.3 g) by chromatography.

2 The title material is prepared from 2A by the method described in Example 1.

EXAMPLE 3

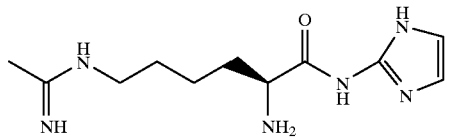

2S-amino-6-[(1-iminoethyl)amino]-N-(1H-imidazol-2-yl)hexanamide, dihydrochloride 3 The title material was prepared in the same manner as 1 starting from 2-aminoimidazole.

EXAMPLE 4

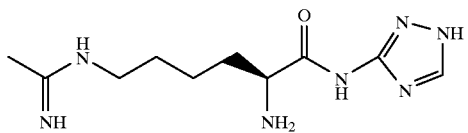

2S-amino-6-[(1-iminoethyl)amino]-N-(1H-1,2,4-triazol-3-yl)hexanamide, dihydrochloride 4 The title material is prepared in the same manner as 1 starting from 3-aminotriazole.

EXAMPLE 5

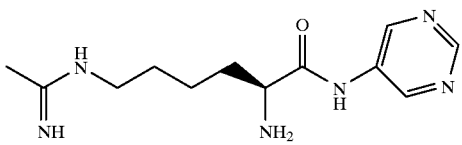

2S-amino-6-[(1-iminoethyl)amino]-N-(5-pyrimidinyl)hexanamide, hydrate, dihydrochloride 5 The title material is prepared in the same manner as 1 starting from 5-aminopyrimidine.

EXAMPLE 6

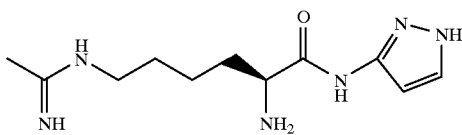

2S-amino-6-[(1-iminoethyl)amino]-N-(1H-pyrazol-3-yl)hexanamide, hydrate, dihydrochloride 6 The title material is prepared in the same manner as 1 starting from 3-aminopyrazole.

EXAMPLE 7

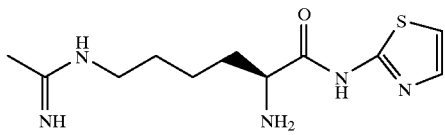

2S-amino-6-[(1-iminoethyl)amino]-N-(thiazol-2-yl)hexanamide, dihydrochloride

7 The title material was prepared in the same manner as 1 starting from 2-aminothiazole.

Biological Data

The activity of the above listed compounds as NO synthase inhibitors is determinable in the following assays:

Citrulline Assay for Nitric Oxide Synthase

Nitric oxide synthase activity was measured by monitoring the conversion of L-[2,3-3H]-arginine to L-[2,3-3H]-citrulline (1,2). Human inducible NOS (hiNOS), human endothelial constitutive NOS (hecNOS) and human neuronal constitutive NOS (hncNOS) were each cloned from RNA extracted from human tissue. The recombinant enzymes were expressed in insect cells using a baculovirus vector. Enzyme activity was isolated from cell extracts and partially purified by DEAE-Sepharose chromatography (2). Enzyme and inhibitors were added to give a volume of 50 μL in 50 mM Tris (pH 7.6) and the reaction initiated by the addition of 50 μL of a solution containing 50 mM Tris (pH 7.6), 2.0 mg/mL bovine serum albumin, 2.0 mM DTT, 4.0 mM CaCl2, 20 μM FAD, 100 μM tetrahydrobiopterin, 0.4–2.0 mM NADPH and 60 μM L-arginine containing 0.9 μCi of L-[2,3-3H]-arginine. For constitutive NOS, calmodulin was included at a final concentration of 40–100 nM. Following incubation at 37° C. for 15 minutes, the reaction was terminated by addition of 300 μL cold buffer containing 10 mM EGTA, 100 mM HEPES (pH5.5) and 1.0 mM L-citrulline. The [3H]-citrulline was separated by chromatography on Dowex 50W X-8 cation exchange resin and radioactivity quantified with a liquid scintillation counter.

1. Bredt, D. S. and Snyder, S. H. (1990) Proc. Natl. Acad. Sci. U.S.A. 87, 682–685.
2. Misko, T. P., Moore, W. M., Kasten, T. P., Nickols, G. A., Corbett, J. A., Tilton, R. G., McDaniel, M. L., Williamson, J. R. and Currie, M. G. (1993) Eur. J. Pharm. 233, 119–125.

TABLE 1

| Example No. | hiNOS (IC$_{50}$ in μM) | hecNOS (IC$_{50}$ in μM) | Selectivity |
|---|---|---|---|
| 1 | 21.4 | 2425 | 113 |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having the formula;

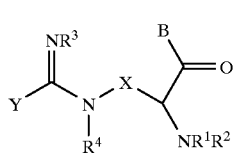

(I)

or a pharmaceutically acceptable salt thereof;
wherein;

$R^1$, $R^2$ are independently selected from the group consisting of hydrogen, lower alkyl, lower alkenyl and lower alkynyl;

$R^3$, $R^4$ are independently selected from the group consisting of hydrogen, lower alkyl, lower alkenyl, lower alkynyl, OR$^6$ where R$^6$ is hydrogen, lower alkyl, lower alkenyl, lower alkynyl, aryl, COR$^7$, or SO$_2$R$^8$ where R$^7$ and R$^8$ are independently selected from the group consisting of lower alkyl, lower alkenyl, lower alkynyl and aryl;

X is selected from the group consisting of lower alkylene, lower alkenylene, and lower alkynylene all of which may be optionally substituted with lower alkyl, lower alkoxy, hydroxy, halogen, trifluoromethyl, nitro, cyano, amino;

Y is selected from the group consisting of lower alkyl, lower alkenyl, and lower alkynyl or Y can be NR$^9$R$^{10}$ wherein R$^9$ and R$^{10}$ are independently selected from the group consisting of hydrogen, lower alkyl, lower alkenyl, lower alkynyl, nitro, amino, aryl, and lower alkaryl; and B is NR$^5$R$^{11}$ wherein R$^5$ is selected from the group consisting of hydrogen, lower alkyl, lower alkenyl, lower alkynyl and aryl, and R$^{11}$ is selected from a 3 to 8 member heterocyclyl radical in which at least one member of the ring is carbon and in which 1 to about 4 members are heteroatoms independently selected from oxygen, nitrogen and sulfur and said heterocyclyl radical may be optionally substituted with hydroxyl, lower alkoxy, lower alkyl, halogen, nitro, carboxyl, SO$_2$R$^{13}$ where R$^{13}$ is selected from lower alkyl, lower alkoxy, NR$^1$R$^2$, amino, acyloxy, trifluoromethyl, phenyl and naphthyl which may be optionally substituted with halogen, nitro, lower alkoxy, and lower alkyl.

2. A compound having the formula;

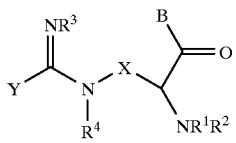
(I)

or a pharmaceutically acceptable salt thereof;
wherein;

$R^1$, $R^2$ are independently selected from the group consisting of hydrogen, lower alkyl, lower alkenyl and lower alkynyl;

$R^3$, $R^4$ are independently selected from the group consisting of hydrogen, lower alkyl, lower alkenyl, lower alkynyl, $OR^6$ where $R^6$ is hydrogen, lower alkyl, lower alkenyl, lower alkynyl, aryl, $COR^7$, or $SO_2R^8$ where $R^7$ and $R^8$ are independently selected from the group consisting of lower alkyl, lower alkenyl, lower alkynyl and aryl;

X is selected from the group consisting of lower alkyl having from one to six carbon atoms, lower alkenyl having from two to six carbon atoms, and lower alkynyl having from two to six carbon atoms which may be optionally substituted with lower alkyl, lower alkoxy, hydroxy, halogen, trifluoromethyl, nitro, cyano, amino;

Y is selected from the group consisting of lower alkyl, lower alkenyl, and lower alkynyl or Y can be $NR^9,R^{10}$ wherein $R^9$ and $R^{10}$ are independently selected from the group consisting of hydrogen, lower alkyl, lower alkenyl, lower alkynyl, nitro, amino, aryl, and lower alkaryl; and B is $NR^5R^{11}$ wherein $R^5$ is selected from the group consisting of hydrogen, lower alkyl, lower alkenyl, lower alkynyl and aryl, and $R^{11}$ is selected from a 3 to 8 member heterocyclyl radical in which at least one member of the ring is carbon and in which 1 to about 4 members are heteroatoms independently selected from oxygen, nitrogen and sulfur and said heterocyclyl radical may be optionally substituted with hydroxyl, lower alkoxy, lower alkyl, halogen, nitro, carboxyl, amino, acyloxy, trifluoromethyl, phenyl and naphthyl which may be optionally substituted with halogen, nitro, lower alkoxy, and lower alkyl.

3. The compound as recited in claim 2 wherein
$R^1$, $R^2$ are independently selected from the group consisting of hydrogen, lower alkyl, lower alkenyl and lower alkynyl;

$R^3$, $R^4$ are independently selected from the group consisting of hydrogen, lower alkyl, lower alkenyl, lower alkynyl, $OR^6$ where $R^6$ is hydrogen, lower alkyl, lower alkenyl, lower alkynyl, or aryl, $COR^7$, $SO_2R^8$ where $R^7$ and $R^8$ are independently selected from the group consisting of lower alkyl, lower alkenyl, lower alkynyl and aryl;

X is selected from the group consisting of lower alkyl having from two to six carbon atoms, lower alkenyl having from two to six carbon atoms, and lower alkynyl having from two to six carbon atoms which may be optionally substituted with lower alkyl, lower alkoxy, hydroxy, halogen, trifluoromethyl, nitro, cyano, amino;

Y is selected from the group consisting of lower alkyl, lower alkenyl, lower alkynyl or Y can be $NR^9,R^{10}$ wherein $R^9$ and $R^{10}$ are independently selected from the group consisting of hydrogen, lower alkyl, lower alkenyl, lower alkynyl, nitro, amino, and lower alkylaryl; and B is $NR^5R^{11}$ wherein $R^5$ is selected from the group consisting of hydrogen, lower alkyl, lower alkenyl, and lower alkynyl, and $R^{11}$ is selected from a 5 to 6 member heterocyclyl radical in which 1 to 4 heteroatoms are independently selected from oxygen, nitrogen and sulfur and said heterocyclyl radical can be optionally substituted with lower alkoxy, lower alkyl, halogen, nitro, carboxyl, trifluoromethyl, and amino.

4. The compound as recited in claim 3 wherein
$R^1$, $R^2$ are independently selected from the group consisting of hydrogen and lower alkyl;

$R^3$, $R^4$ are independently selected from the group consisting of hydrogen, lower alkyl, lower alkenyl, lower alkynyl;

X is selected from the group consisting of lower alkyl having from two to six carbon atoms, lower alkenyl having from two to six carbon atoms, and lower alkynyl having from two to six carbon atoms which may be optionally substituted with lower alkyl, lower alkoxy, hydroxy, halogen, trifluoromethyl, nitro, cyano, amino;

Y is selected from the group consisting of lower alkyl, lower alkenyl, lower alkynyl or Y can be $NR^9,R^{10}$ wherein $R^9$ and $R^{10}$ are independently selected from the group consisting of hydrogen, alkyl, lower alkenyl, lower alkynyl, nitro, amino, and lower alkylaryl; and B is $NR^5R^{11}$ wherein $R^5$ is selected from the group consisting of hydrogen, lower alkyl, lower alkenyl, and lower alkynyl, $R^{11}$ is selected from a 5 to 6 member heterocyclyl radical in which 1 to 4 heteroatoms are nitrogen or sulfur, and said heterocyclyl radical can be optionally substituted with hydroxyl, lower alkoxy, lower alkyl, halogen, nitro, and carboxyl.

5. The compound as recited in claim 4 wherein
$R^1$, $R^2$ are hydrogen;
$R^3$, $R^4$ are hydrogen;
X is selected from the group consisting of lower alkyl, lower alkenyl, and lower alkynyl;
Y is selected from the group consisting of lower alkyl or Y can be $NR^9,R^{10}$ wherein $R^9,R^{10}$ are independently selected from the group consisting of hydrogen, alkyl, lower alkenyl, lower alkynyl, nitro, amino, and lower alkylaryl; and
B is $NR^5R^{11}$ wherein $R^5$ is selected from the group consisting of hydrogen or lower alkyl, $R^{11}$ is selected from a 5 to 6 member heterocyclyl radical in which 1 to 4 heteroatoms are nitrogen or sulfur.

6. A compound as recited in claim 5 wherein said compound is selected from the group consisting of;
2S-amino-6-[(1-iminoethyl)amino]-N-(1H-tetrazol-5-yl) hexanamide, hydrate, dihydrochloride;
2S-amino-5-[[amino(nitroimino)methyl]amino]-N-(1H-tetrazol-5-yl)pentanamide, hydrochloride;
2S-amino-6-[(1-iminoethyl)amino]-N-(1H-imidazol-2-yl) hexanamide, dihydrochloride;
2S-amino-6-[(1-iminoethyl)amino]-N-(1H-1,2,4-triazol-3-yl)hexanamide, dihydrochloride;
2S-amino-6-[(1-iminoethyl)amino]-N-(5-pyrimidinyl) hexanamide, hydrate, dihydrochloride;
2S-amino-6-[(1-iminoethyl)amino]-N-(1H-pyrazol-3-yl) hexanamide, hydrate, dihydrochloride; and
2S-amino-6-[(1-iminoethyl)amino]-N-(thiazol-2-yl) hexanamide, dihydrochloride.

7. A method of inhibiting nitric oxide synthesis in a subject in need of such inhibition by administering a therapeutically effective amount of a compound of claims 1, 2, 3, 4, 5 or 6.

8. A method of selectively inhibiting nitric oxide synthesis produced by inducible NO synthase over nitric oxide produced by the constitutive forms of NO synthase in a subject in need of such selective inhibition by administering a therapeutically effective amount of a compound of claims 1, 2, 3, 4, 5 or 6.

9. A method of lowering nitric oxide levels in a subject in need of such by administering a therapeutically effective amount of a compound of claims 1, 2, 3, 4, 5 or 6.

10. A pharmaceutical composition comprising a compound of claims 1, 2, 3, 4, 5 or 6 together with one or more pharmaceutically acceptable carriers.

* * * * *